Figure 8:
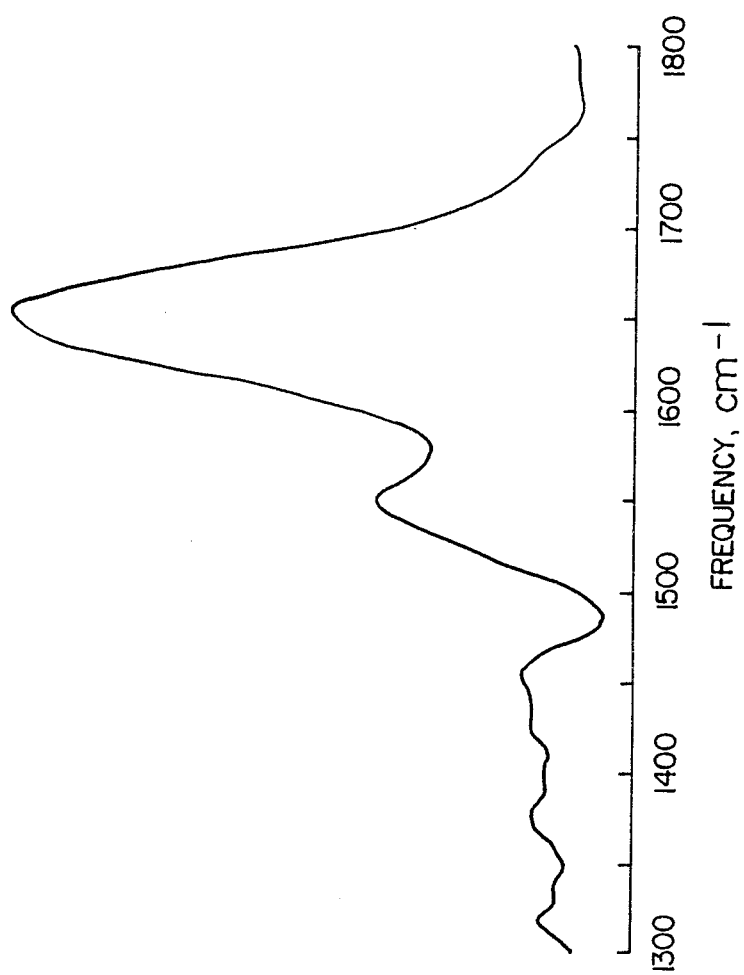

United States Patent [19]

Wong

[11] Patent Number: 4,980,551
[45] Date of Patent: Dec. 25, 1990

[54] NON-PRESSURE-DEPENDANCY INFRARED ABSORPTION SPECTRA RECORDING, SAMPLE CELL

[75] Inventor: Patrick T. T. Wong, Ottawa, Canada

[73] Assignee: National Research Council Canada Conseil national de recherches Canada, Ottawa, Canada

[21] Appl. No.: 461,182

[22] Filed: Jan. 5, 1990

[51] Int. Cl.$^5$ .......................... G01J 5/04; G01J 5/06; G01J 5/08
[52] U.S. Cl. .................................. 250/338; 250/343; 356/244; 356/440
[58] Field of Search .................... 250/338.1, 343, 440, 250/244; 356/440, 244

[56] References Cited

U.S. PATENT DOCUMENTS

| | | | |
|---|---|---|---|
| 3,521,963 | 7/1970 | Bader | 356/244 |
| 4,095,105 | 6/1978 | Rosenthal | 250/338.1 |
| 4,286,881 | 9/1981 | Janzen | 356/440 |
| 4,678,913 | 7/1987 | Dodd, Jr. et al. | 250/341 |

OTHER PUBLICATIONS

Pattison et al., A Sample Cell for Low Temperature Optical Absorption Studies of Frozen Aqueous Solutions, Rev. Sci. Instrum. vol. 45, No. 2, 2/74, pp. 304–305.

Primary Examiner—Constantine Hannaher
Assistant Examiner—Jacob M. Eisenberg
Attorney, Agent, or Firm—Francis W. Lemon

[57] ABSTRACT

A non-pressure-dependancy infrared absorption spectra recording, sample holder comprises a sample holder having an infrared light beam transmitting passage, two windows of infrared light transmitting material in the passage in face-to-face contact, with at least one window having an inner surface portion contoured to provide between the windows a sample space shaped to provide adjacent light beam paths which are different in length and a clamp for resiliently clamping the windows in the sample holder. A deformable sample is lightly compressed to fill the sample space, and an infrared light beam is passed through the sample. The adjacent light beam paths being of different lengths avoids optical interference fringes so that absorption spectra of the sample can be recorded.

4 Claims, 2 Drawing Sheets

U.S. Patent     Dec. 25, 1990     Sheet 1 of 2     4,980,551
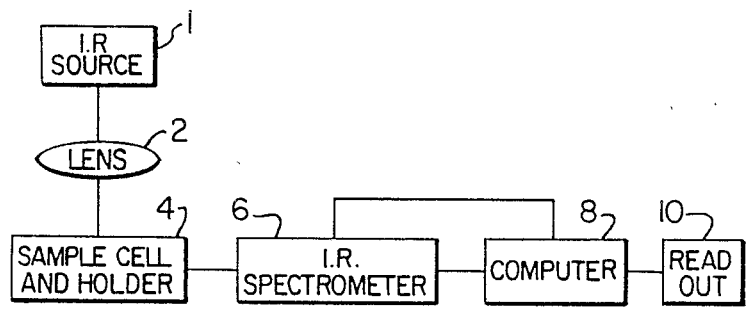
FIG. 1
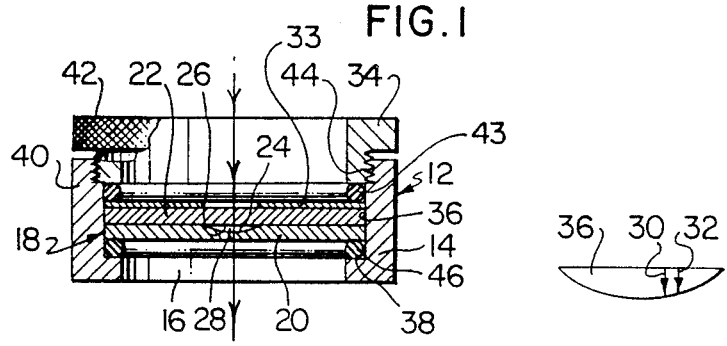
FIG. 2                FIG. 3
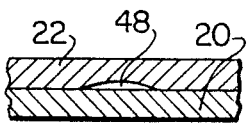    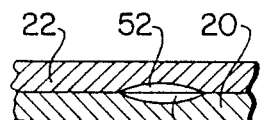
FIG. 4                FIG. 5
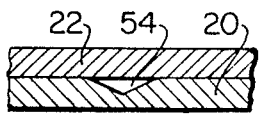    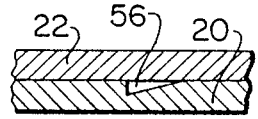
FIG. 6                FIG. 7

NON-PRESSURE-DEPENDANCY INFRARED ABSORPTION SPECTRA RECORDING, SAMPLE CELL

This invention relates to a non-pressure-dependancy infrared absorption spectra recording, sample cell.

It has been proposed in U.S. Pat. No. 4,678,913, dated July 7, 1987, "Method and Apparatus for Analyzing the Nature of a Sample", J. G. Dodd, Jr., and J. J. Dodd, to seal a minute sample in a passage through a carrier, between two lenses, for analyzing the absorption spectra of the sample.

It has also been proposed in U.S. Pat. No. 4,286,881, dated September 1, 1981, "Sample Cell", J. Janzen, to squeeze a semi-solid sample between two lenses to a predetermined thickness in order to obtain optical measurements of the sample.

While the proposals of J. G. Dodd et al and J. Janzen are useful, there is a need for a sample Cell in which deformable samples of substances having a relatively high infrared absorption can be used without interference fringes being present.

According to the present invention there is provided a non-pressure-dependancy infrared absorption spectra recording, sample cell, comprising:
  (a) a sample holder having:
    (i) an infrared light beam transmitting passage extending therethrough, and
    (ii) a window locating means in the passage, the means being for locating a pair of windows in face-to-face contact across the passage, and
  (b) a pair of windows of infrared light transmitting material for location in the passage, by the locating means, in face-to-face contact, the windows having facing surfaces shaped to provide a sample space therebetween in the path of the light beam transmitting passage, the sample space having a shape which provides adjacent, infrared light beam paths therethrough which are different in length, and
  (c) masking means for restricting the entry of infrared light only to those portions of the windows having the sample space therebetween, and
  (d) means for resiliently urging the windows into face-to-face contact in the passage, whereby, in operation,
  (e) with the pair of windows located and urged into face-to-face contact in the passage, and a deformable sample lightly compressed in the sample space to substantially conform to the shape thereof, the passage of a condensed, infrared light beam through the sample, along the adjacent light paths of different lengths, will avoid introducing optical interference fringes in the infrared spectra, and the high quality infrared absorption spectra of the sample will be readily obtained.

The sample space may be in the form of a segment of a sphere.

The lower one of the windows may have a concavity forming the sample space, and an upper one of the windows may have a plane surface sealing the cavity.

The windows may be of a substance selected from the group consisting of NaCl, KBr, BaF$_2$, CaF$_2$, AgCl, ZnTe, CsI, TlI-TlBr mixture, ZnS and MgO.

In some embodiments of the present invention, the window locating means comprises a recess and a shoulder in the passage, the means for urging the windows into face-to-face contact comprises an externally screw threaded clamping ring which screws into a screw threaded portion of the passage, and a ring seal is provided on the shoulder against which the windows are to be urged into face-to-face contact by the clamping ring.

In the accompanying drawings which illustrate, by way of example, embodiments of the present invention, FIG. 1 is a block diagram of a non-pressure-dependancy infrared absorption, spectroscopic apparatus, FIG. 2 is an enlarged, partly sectional side view of the sample cell shown in FIG. 1, FIG. 3 is an even more enlarged side view of the sample space shown in FIG. 2, FIGS. 4 to 7 are scrap, sectional side views of windows providing sample spaces of different shapes to that shown in FIGS. 2 and 3, and FIG. 8 shows the infrared absorption spectrum of rat liver tissue using the apparatus shown in FIGS. 1 to 3.

In FIGS. 1 and 2 there is shown an infrared light beam source 1, a convex lens 2, a sample cell and assembly holder generally designated 4, an infrared spectrometer 6, a computer 8, and a read-out 10.

As shown in FIG. 2, the sample cell, generally designated 12, of the sample cell and assembly holder 4, comprises:
  (a) a sample holder 14 having:
    (i) an infrared light beam transmitting passage 16 extending therethrough, and
    (ii) a window locating means, generally designated 18, in the passage 16, the window locating means being for locating a pair of windows in face-to-face contact across the passage 16, and
  (b) a pair of windows of infrared light transmitting material 20 and 22 for location in the passage 16, by the locating means 18, in face-to-face contact, the windows 20 and 22 having inner facing surface portions, 24 and 26 respectively, shaped to provide a sample space 28 therebetween in the path of the light beam transmitting passage 16, the sample space having a shape, as shown in FIG. 3, which provides adjacent light paths, such as light paths 30 and 32 which are different in length,
  (c) masking means 33 for restricting the entry of infrared light only to those portions of the windows 20 and 22 having the sample space 28 therebetween, and
  (d) means 34 for resiliently urging the windows 20 and 22 into face-to-face contact in the passage 16.

The infrared light beam source 1 may be any conventional infrared light beam source.

The sample holder 14, which in this embodiment is cylindrical, may be made of, for example, metal or plastic.

The window locating means 18 comprises a recess 36 in the passage 16 and a shoulder 38.

The windows 20 and 22 may be of NaCl, KBr, BaF$_2$, CsI, CaF$_2$, AgCl, ZnTe, MgO, KRS-5 ® or Irtran 1-6 ®.

The masking means 33 may comprise a coating on the window 22, a disk of, for example, metal or plastic, or an inner portion of the means 34. If the masking means 33 is of a resilient material it may also provide a resilient member between the means 34 and the window 22.

The means 34 for urging the windows 20 and 22 into face-to-face contact in the passage 16, comprises an externally screw threaded clamping ring 40, having a knurled flange portion 42, and a resilient 0-ring 43 between the clamping ring 40 and the windows 20 and 22. The screw threaded clamping ring 40 is screwed into a screw threaded portion 44 of the passage 16 to compress the 0-ring 43 and to resiliently urge the windows 20 and 22 into face-to-face contact against a resilient 0-ring 46 which is pressed against the shoulder 38. As previously stated, the masking means may also comprise the ring 43.

In operation, the pair of windows 20 and 22 are located and urged into face-to-face contact in the passage 16, as shown in FIG. 2, and the deformable sample 36 is lightly compressed in the sample space 28 to substantially conform to the shape thereof. The passage of a condensed, infrared light beam through the sample 36, from the source 1 (FIG. 1) through the lens 2, along the adjacent light beam paths, such as 30 and 32 (FIG. 3), avoids introducing optical interference fringes in the infrared spectra, and the high quality infrared spectra of the sample is readily recorded by the infrared spectrometer 6. These spectra obtained by the spectrometer 6 are analyzed by the computer to determine, for example, molecular characterization of the sample 36.

In an example of tests made to verify the present invention, using the apparatus shown in FIGS. 1 to 3, the infrared absorption spectra were recorded for rat liver tissues.

The results are shown in FIG. 8.

In FIGS. 4 to 7, similar parts to those shown in FIGS. 1 to 3 are designated by the same reference numerals and the previous description is relied upon to describe them.

In FIG. 4, the uppermost window 22 is provided with a concavity 48 while the lower window 20 has a plane surface.

In FIG. 5, both of the windows 20 and 22 are provided with concavities 50 and 52 respectively.

In FIG. 6, the window 20 is provided with an inverted-cone-shaped cavity 54 while the uppermost window 22 has a plane surface.

In FIG. 7, the window 20 is provided with a wedge-shaped cavity 56 while the uppermost window 22 has a plane surface.

The present invention is particularly useful for analyzing organ tissue, for example, liver, kidney, muscle, brain tissue, and so forth in its original form which, prior to the present invention, had to be dried or mashed for analysis.

The present invention may be used to analyze other deformable, semi-solid material, for example, gels, amorphous polymers and highly viscous liquid.

I claim:

1. A non-pressure-dependancy infrared absorption spectra recording, sample cell, comprising:

(a) a sample holder having:
      (i) an infrared light beam transmitting passage extending therethrough, and
      (ii) a window locating means in the passage, the means being for locating a pair of windows in face-to-face contact across the passage, and
   (b) a pair of windows of infrared light transmitting material for location in the passage, by the locating means, in face-to-face contact, the windows having inner facing surface portions shaped to provide a sample space therebetween in the path of the light beam transmitting passage, the sample space having a shape which provides adjacent, infrared light beam paths therethrough which are different in length,
   (c) masking means for restricting the entry of infrared light only to those portions of the windows having the sample space therebetween,
   (d) means for resiliently urging the windows into face-to-face contact in the passage, whereby, in operation,
   (e) with the pair of windows located and urged into face-to-face contact in the passage, and a deformable sample lightly compressed in the sample space to substantially conform to the shape thereof, the passage of a condensed, infrared light beam through the sample, along the adjacent light paths of different lengths, will avoid introducing optical interference fringes in the infrared spectra, and the high quality infrared absorption spectra of the sample will be readily obtained.

2. A sample cell according to claim 1, wherein the sample space is in the form of a segment of a sphere.

3. A sample cell according to claim 1, wherein the window panes are of a substance selected from the group consisting of NaCl, KBr, $BaF_2$, $CaF_2$, AgCl, ZnTe, MgO, TlI-TlBr mixture, CsI and ZnS.

4. A sample cell according to claim 1, wherein the window locating means comprises a recess and a shoulder in the passage, the means for resiliently urging the windows into face-to-face contact comprises an externally screw threaded clamping ring which screws into a screw threaded portion of the passage, and a resilient ring between the clamping ring and the windows, and a further resilient ring is provided on the shoulder against which the windows are to be urged into face-to-face contact by the clamping ring.

* * * * *